(12) United States Patent
Norstrom et al.

(10) Patent No.: US 10,271,775 B2
(45) Date of Patent: Apr. 30, 2019

(54) DETERMINING PERFORMANCE INDICATORS FOR PERIODIC MOVEMENTS

(71) Applicant: WEMEMOVE AB, Kista (SE)

(72) Inventors: Christer Norstrom, Torshalla (SE); Anders Holst, Taby (SE); Magnus Jonsson, Stockholm (SE)

(73) Assignee: WEMEMOVE AB, Kista (SE)

( * ) Notice: Subject to any disclaimer, the term of this patent is extended or adjusted under 35 U.S.C. 154(b) by 416 days.

(21) Appl. No.: 14/906,093

(22) PCT Filed: Jul. 4, 2014

(86) PCT No.: PCT/SE2014/050859
§ 371 (c)(1),
(2) Date: Jan. 19, 2016

(87) PCT Pub. No.: WO2015/009228
PCT Pub. Date: Jan. 22, 2015

(65) Prior Publication Data
US 2016/0192866 A1    Jul. 7, 2016

(30) Foreign Application Priority Data
Jul. 18, 2013    (SE) ..................... 1350894

(51) Int. Cl.
*A61B 5/11* (2006.01)
*G06K 9/00* (2006.01)
(Continued)

(52) U.S. Cl.
CPC ........ *A61B 5/1123* (2013.01); *A63B 24/0006* (2013.01); *G01P 15/02* (2013.01);
(Continued)

(58) Field of Classification Search
CPC ............. A61B 5/1123; A61B 2503/10; A61B 2562/0219; A61B 5/1118; A61B 5/02438;
(Continued)

(56) References Cited

U.S. PATENT DOCUMENTS 6,522,266 B1 * 2/2003 Soehren ............... A61B 5/7264
340/988
6,720,984 B1 * 4/2004 Jorgensen ............... G06F 3/015
600/300
(Continued)

FOREIGN PATENT DOCUMENTS

EP    2 624 171 A2    8/2013

OTHER PUBLICATIONS

Stauffer Y et al.: "Multi sensor,accelerometer based nordic skiing analysis: Hardware development, testing and preliminary results", 5th European Conference of the International Federation for Medical and Biological Engineering: Sep. 14-18, 2011, Budapest, Hungary; [IFMBE Proceedings; ISSN 1680-0737; vol. 37]. Springer Verlag, DE, vol. 37, No. Pt. 2, Oct. 14, 2011, pp. 818-821 XP008173002.
(Continued)

*Primary Examiner* — Jerry-Daryl Fletcher
(74) *Attorney, Agent, or Firm* — Young & Thompson

(57) ABSTRACT

A method for determining a value of a performance indicator for a periodic movement performed by a human or an animal. The method includes receiving (210) time series data from an inertial sensor used for sensing the periodic movement, partitioning (220) the received time series data into periods of the movement, and transforming (230) the time series data of each period into a data representation of a defined size. The method further includes classifying (240) each period into a movement class, and determining (250) a value of a performance indicator for at least one period of
(Continued)

the movement, based on the data representation and on the movement class of the at least one period.

20 Claims, 12 Drawing Sheets

(51) Int. Cl.
*A63B 24/00* (2006.01)
*G01P 15/02* (2013.01)
*G09B 19/00* (2006.01)
*G01P 15/00* (2006.01)

(52) U.S. Cl.
CPC ....... *G06K 9/00342* (2013.01); *G09B 19/003* (2013.01); *A61B 2503/10* (2013.01); *A61B 2503/40* (2013.01); *G01P 15/00* (2013.01)

(58) Field of Classification Search
CPC ..... A61B 5/11; A61B 5/7264; A61B 2503/40; A61B 5/7267; G06F 17/30811; A63B 2024/0012; A63B 24/0006; A63B 2220/836; A63B 24/0062; A63B 2024/0025; A63B 2220/803; A63B 2220/806; G09B 19/0038; G09B 19/003; G09B 5/02; G06Q 10/0639
See application file for complete search history.

(56) References Cited

U.S. PATENT DOCUMENTS

| | | | |
|---|---|---|---|
| 7,264,554 B2* | 9/2007 | Bentley ............... | A61B 5/1122 382/107 |
| 2002/0052541 A1* | 5/2002 | Cuce .................... | A61B 5/1118 600/300 |
| 2003/0046018 A1* | 3/2003 | Kohlmorgen ........ | G06K 9/6228 702/127 |
| 2013/0053990 A1* | 2/2013 | Ackland ............... | G06Q 30/02 700/91 |

OTHER PUBLICATIONS

Myong-Woo Lee et al.: "A single tri-axial accelerometer-based real-time personal life log system capable of activity classification and exercise information generation", 2010 Annual International Conference of the IEEE Engineering in Medicine and Biology Soc! Ety : ( EMBS 2010) ; Buenos Aires, Argentina, Aug. 31-Sep. 4, 2010, IEEE, Piscataway, NJ, USA, Aug. 31, 2010, pp. 1390-1393, XP032108697.

Anders Holst et al.: "Classification of movement patterns in skiing", Twelfth Scandinavian Conference on Artificial Intelligence: SCA! 2013, Amsterdam : IOS Press, 2013, NL, vol. 257, Nov. 20, 2013 (Nov. 20, 2013), pp. 115-124, XP008172989.

Havard Myklebust et al.: "Morpho logical analysis of acceleration signals in cross-country skiing", Proceedings of Biosignals—International Conference on Bio-Inspired Systems and Signal Processing (BIOSTEC 2011), 2011, pp. 510-517, XP055149922, the whole document.

Finn Marsland et al.: "Identification of Cross-Country Skiing Movement Patterns Using Micro-Sensors", Sensors, vol. 12, No. 4, Apr. 18, 2012 (Apr. 18, 2012) , pp. 5047-5066, XP055149753, DOI: 10.33901s120405047 Sects. I, 2.2, 2.5 Sects. 3.2.1, 3.4.

Thomas Homewood et al.: "Skitracker: Measuring Skiing Performance using a Body Area Network", IT 13014, Feb. 28, 2013 (Feb. 28, 2013), pp. 1-107, XP055150326, Uppsala, Sweden Retrieved from the Internet: [retrieved on Oct. 31, 2014] pp. 10-13 pp. 39-45.

Gerald Hurst E: "Bayesian Autoregressive Time Series Analysis", IEEE Transactions on Systems Science and Cybernetics, IEEE, US, vol. I, No. 3, Sep. 1968 (Sep. 1968), pp. 317-324, XP011163336, ISSN: 0536-1567 abstract.

Hsing-Kuo Pao et al.: "Trajectory Based Behavior Analysis for User Verification", Intelligent Data Engineering and Automated Learning (IDEAL 2010), vol. 6283, Sep. 2010 (Sep. 2010), pp. 316-323, XP019149658, ISBN: 978-3-642-15380-8 Sect. 3.2.

Andrea Mannini et al.: "Machine Learning Methods for Classifying Human Physical Activity from On-Body Accelerometers", Sensors, vol. 10, No. 2, Feb. 2010 (Feb. 2010), pp. 1154-1175, XP055149795, Sects. 2.5, 2.6, 3.4.

International Search Report, dated Nov. 12, 2014, from corresponding PCT application.

* cited by examiner though. More particularly, the disclosure relates to a system and a method for determining a value of a performance indicator for a periodic movement performed by a human or an animal.

DETERMINING PERFORMANCE INDICATORS FOR PERIODIC MOVEMENTS

TECHNICAL FIELD

The disclosure relates to performance of movements performed by a human or animal. More particularly, the disclosure relates to a system and a method for determining a value of a performance indicator for a periodic movement performed by a human or an animal.

BACKGROUND

Many professional athletes, but also joggers or persons performing other physical exercises use pulse watches as a training aid today. The pulse watches may also incorporate positioning systems for collecting more sophisticated information during exercise. However, the pulse watches still provide a limited amount of information, and does not provide any information about how a physical exercise or movement is performed. Different tools based on video analysis are used in many sports for post hoc analysis of movements and physical exercises. Such tools may comprise everything from simple systems based on consumer cameras with graphic annotation interfaces, to considerably more complex and expensive motion-capture systems for more precise three dimensional modeling of movements. A drawback of such tools is that the feedback is provided only after the exercise, and that it may be difficult to observe small differences between movements performed by the athlete. Furthermore, the tools based on video analysis are difficult to use in a sport such as cross-country skiing or running, as the athlete is moving over a large area during the exercise, and it may be difficult to capture every movement with a camera.

Another type of tools for analysis of an athlete's movements is based on the use of sensors placed on different parts of the athlete's body, where the sensors typically communicate wirelessly with a computer. The sensors may capture data which may be difficult for a trainer to see with his own eyes. The computer may thus capture data from the sensors on the athlete's body during the exercise, and the captured data may then be used in an analysis tool on the computer to analyze the athlete's performance and movements. The analysis can be used e.g. as a training aid to improve the performance of the athlete. However, a great number of sensors may be needed to get a useful result, and they may interfere with the athlete's movements during the exercise. Furthermore, even if the data capture is performed during the exercise, it may still be complex and time consuming to analyze the large amount of data that is collected and to provide relevant and understandable feedback in real-time during the exercise.

SUMMARY

It is therefore an object to address some of the problems outlined above, and to provide a solution providing values of performance indicators determined for a periodic movement performed by e.g. an athlete, without hindering or restricting the athlete's movements, such that accurate and relevant feedback regarding the athlete's performance can be given in real time. This object and others are achieved by the method and the system according to the independent claims, and by the embodiments according to the dependent claims.

In accordance with a first embodiment, a method for determining a value of a performance indicator for a periodic movement performed by a human or an animal is provided. The method comprises receiving time series data from an inertial sensor used for sensing the periodic movement, partitioning the received time series data into periods of the movement, and transforming the time series data of each period into a data representation of a defined size. The method further comprises classifying each period into a movement class based on the data representations and a statistical model comprising a Markov chain of multivariate Gaussian distributions for each at least one movement class. The method also comprises determining a value of a performance indicator for at least one period of the movement, based on the data representation and on the movement class of the at least one period.

In accordance with a second embodiment, a system for determining a value of a performance indicator for a periodic movement performed by a human or an animal is provided. The system comprises an inertial sensor for sensing the periodic movement, and a communication unit connected to a processing circuit. The communication unit is configured to receive time series data from the inertial sensor. The processing circuit is configured to partition the received time series data into periods of the movement, transform the time series data of each period into a data representation of a defined size, and classify each period into a movement class based on the data representations and a statistical model comprising a Markov chain of multivariate Gaussian distributions for each at least one movement class. The processing circuit is also configured to determine a performance indicator for at least one period of the movement, based on the data representation and on the movement class of the at least one period.

An advantage of embodiments is that only one sensor and limited processor capacity is needed for determining a value of a performance indicator for the periodic movement performed by e.g. an athlete during exercise. A further advantage is that the performance indicator values may be provided in real-time for immediate feedback on the performance.

The risk of disturbing the athlete's movements during the exercise is thus minimized, while still providing accurate and relevant feedback to the athlete in terms of performance indicator values making it possible for the athlete to adapt the movement during the exercise.

Another advantage is that it is easy to compare an athlete's technique and performance during a certain exercise with a previous exercise performed under the same premises. It also enables a comparison between different athletes performances under similar outside conditions.

Other objects, advantages and features of embodiments will be explained in the following detailed description when considered in conjunction with the accompanying drawings and claims.

DETAILED DESCRIPTION

In the following, different aspects will be described in more detail with references to certain embodiments and to accompanying drawings. For purposes of explanation and not limitation, specific details are set forth, such as particular scenarios and techniques, in order to provide a thorough understanding of the different embodiments. However, other embodiments that depart from these specific details may also exist.

Moreover, those skilled in the art will appreciate that the functions and means explained herein below may be implemented using software functioning in conjunction with a programmed microprocessor or general purpose computer, and/or using an application specific integrated circuit (ASIC). It will also be appreciated that while the embodiments are primarily described in the form of a method and a system, they may also be embodied in a computer program product as well as in a system comprising a computer processor and a memory coupled to the processor, wherein the memory is encoded with one or more programs that may perform the functions disclosed herein.

Figure 1:
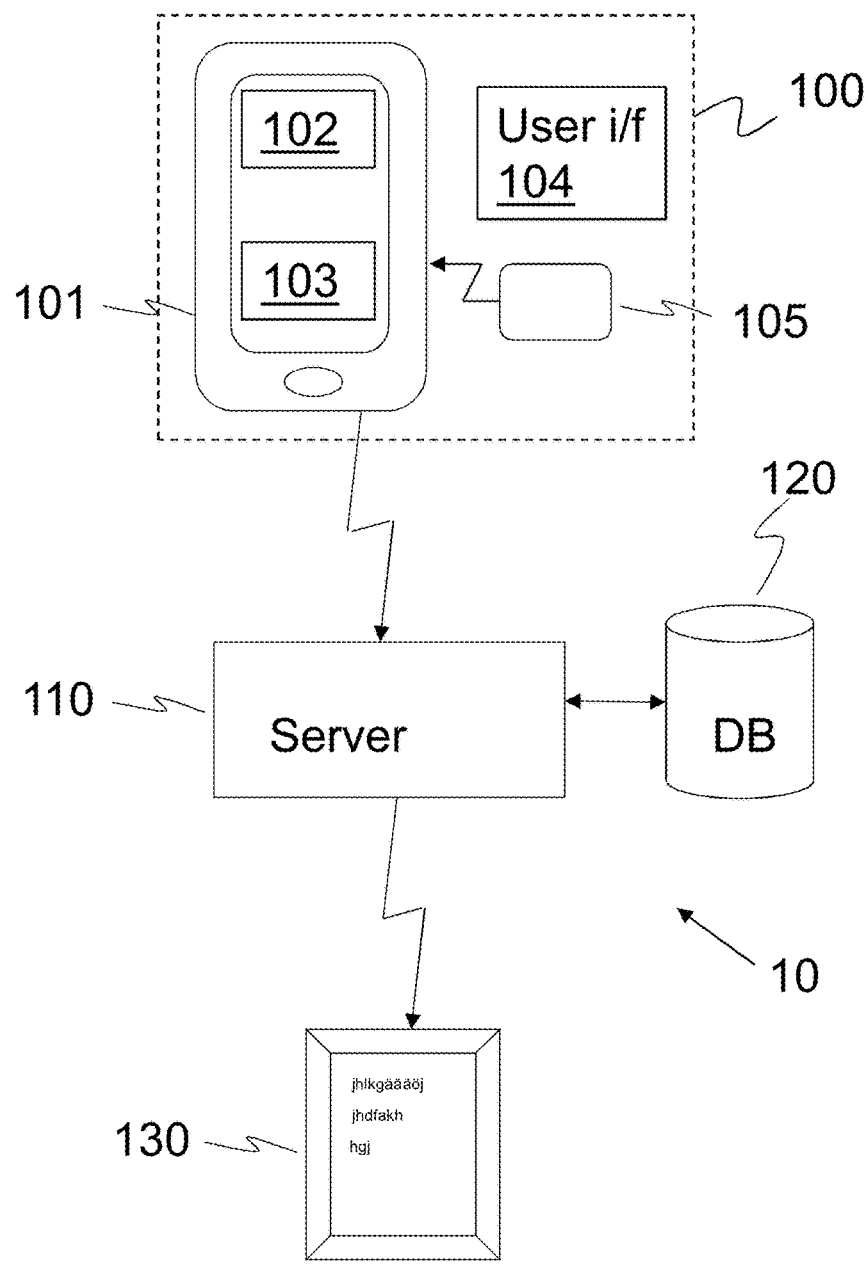
FIG. 1 is a schematic illustration of a system according to one embodiment of the invention.

Embodiments are described in a non-limiting general context in relation to example scenarios where the periodic movement is a movement of an athlete such as a cross-country skier using a classic or skate ski technique or a runner, and with a system according to the one illustrated in FIG. 1, where the sensor is a three-dimensional accelerometer. However, it should be noted that the embodiments may also be applied to other types of periodic movements, such as the periodic movement of a horse, or of a person performing a rehab program movement, and to systems that build on data from other types of sensors such as a one-dimensional accelerometer.

The problem of sensors hindering movement and the inability of determining relevant training aid information in real time from large amounts of streaming data generated by a sensor based system, has been solved by a method where an inertial sensor, such as an accelerometer or a gyroscope, is placed on the body of the skier to sense the periodical ski skating movement of the skier. Streaming data from the sensor is then collected and partitioned into periods of the skier's periodical movement. The data of each period is transformed into a data representation of a defined size, in order to represent each period in a normalized way thus allowing a comparison between periods. The partitioning and the transformation may be referred to as a pre-processing of time series data retrieved from the sensor. The advantage of the pre-processing is that it allows for a data representation in real-time of the periodical movement based on streaming data from an inertial sensor. Furthermore, the data representation is particularly suitable as a basis for classification of movement patterns, as well as for a calculation of different performance indicators for the movement. The data representation may thus be used for a subsequent classification of the periods into a movement class which gives as a result the class of the movement that the skier is performing during a period. Furthermore, based on the pre-processed data representation, and optionally also based on the result from the classification, a value of a performance indicator may be determined. A performance indicator is typically defined as a quantitative or qualitative measurement, or any other criterion, by which the performance, efficiency, or achievement can be assessed, often by comparison with an agreed standard or target. Such a determined performance indicator value may thus be used to evaluate e.g. a performance of the periodic movement performed by a cross-country skier.

In the example of cross-country skiing, different periodic limb-movement patterns are used for different terrain and speeds. A skier may thus be using different periodic movements e.g. depending on if she is skiing uphill or downhill. For classic ski technique, the following ski techniques may be mentioned: diagonal techniques, double poling technique, kick double poling technique, herringbone techniques without a gliding phase, downhill techniques and turning techniques. Each of these ski techniques may correspond to a movement class, and the periodic movement of the skier may thus be classified into one of the ski techniques.

For the example of ski-skating, there is no internationally accepted naming convention for different skating techniques. The following are some examples of the naming of five well defined skating techniques, followed by a brief description of the technique:

1. Gear 1, diagonal V, or single-poling: Similar to the classic herringbone but with a short glide on each ski. This technique is used in very steep uphill.
2. Gear 2, V1, or offset skate: Slightly off-set double-pole on every other leg.
3. Gear 3, V2, or 1-skate: Double-pole on every leg. Used on the flat for accelerating and on moderate uphill.
4. Gear 4, V2 alternate, or 2-Skate: Double-pole on every other leg. Used on the flat, while climbing and on gentle downhill.
5. Gear 5, V skating, or free-skate: Skating without using the poles. Used on downhill at very high speed.

Each defined skating gear may correspond to a movement class, and the periodic movement of the skier may thus be classified into one of the defined skating gears.

When it comes to running, one may e.g. classify the periodic movement of a runner into the movement classes of forefoot-midfoot running and heel-toes running. For the movement of a horse one may think of classifying into the movement classes walking-pace, trotting, and galloping. What movement classes to use may vary depending on what performance indicators that are interesting to determine. Some examples of performance indicators are a propulsion indicator, a level of consistency of the movement, a frequency of movement, and a level of symmetry within a period. These performance indicators will be further described below.

FIG. 1 illustrates a system 10 according to one embodiment of the invention. A unit 100 comprising the inertial sensor 105 connected to a mobile terminal 101, is placed on an athlete. The unit 100 may e.g. be placed on the chest or on the back of the athlete. The mobile terminal 101 comprises a processing circuit 102, and a transmitter 103 for transmitting sensor data to an internet server 110 via a mobile network. The connection between the sensor 105 and the mobile terminal 101 may be a Bluetooth connection, thus making it possible to place the sensor at a distance from the mobile terminal. Furthermore, more than one sensor 105 may be connected to the terminal 101. For example both an accelerometer and a gyroscope may be connected and synchronized with each other. Alternatively two accelerometers placed at different parts of the body may be connected. Today's smart phones have integrated accelerometers and could thus be used as the unit 100 placed on the skier providing a combined sensor 105 and mobile terminal 101. Additional devices such as a Global Positioning System (GPS) receiver device may also be connected to the terminal

101. The server 110 may also be connected to a database (DB) 120 used e.g. for storing data collected from the inertial sensor in the form of raw data or pre-processed data, or for storing results from the classification of the movement and/or performance indicators.

Time series data received from the sensor 105 may be pre-processed and classified locally in the unit 100 carried by the skier, e.g. in the processing circuit 102 of the terminal 101. Time series data may be referred to as a sequence of data received from the sensor 105 over time. An advantage of this embodiment of locally classified data is that performance indicator values may be determined locally and that there is thus no need for the connection to the internet server 110. The system is self-contained. Alternatively, the raw time series data received from the sensor 105 may be transmitted to the server 110, and the pre-processing, the classifying, and the determining of performance indicator values may be performed in the server 110. In the case when no processing of the data is performed in the unit 100 carried by the skier, the unit 100 will only need to comprise the sensor 105 and the transmitter 103 adapted to forward the raw sensor data to the server 110. An advantage of this embodiment is that the unit 100 carried by the skier is reduced to a minimum. A combination is also possible, wherein the pre-processing of the time series data is performed in the unit 100 carried by the skier, and wherein the pre-processed data is transmitted to the server 110 for further classification and determination of performance indicators. An advantage of this embodiment is that the amount of data transmitted between the unit 100 on the skier and the server 110 is reduced compared to if raw sensor data is transmitted to the server 110.

Furthermore, a client or user terminal 130 may be connected to the internet server 110 for visualizing the results from the classification and the performance indicators. Also the visualization could be done in real-time. The client may be connected wirelessly, and used e.g. by a ski trainer following the skier's performance on site by visualizing the classification and performance indicator values in the client user interface. Correspondingly, the unit 100 carried by the skier may also provide a user interface 104 for visualizing the results from the movement analysis in real-time during the exercise. However, for the athlete performing the movement, the user interface would preferably provide audio and/or tactile feedback signals, such that the feedback may be heard or sensed. That would make it possible to receive performance feedback during the exercise while still continuing the training without disturbances. The performance indicator values that are determined during the exercise may thus e.g. be compared to one or more threshold values. A feedback signal may be generated based on the comparison with the threshold(s) and transmitted to the user interface 104 to provide a sound or a touch indicating a certain performance.

Figure 2A:
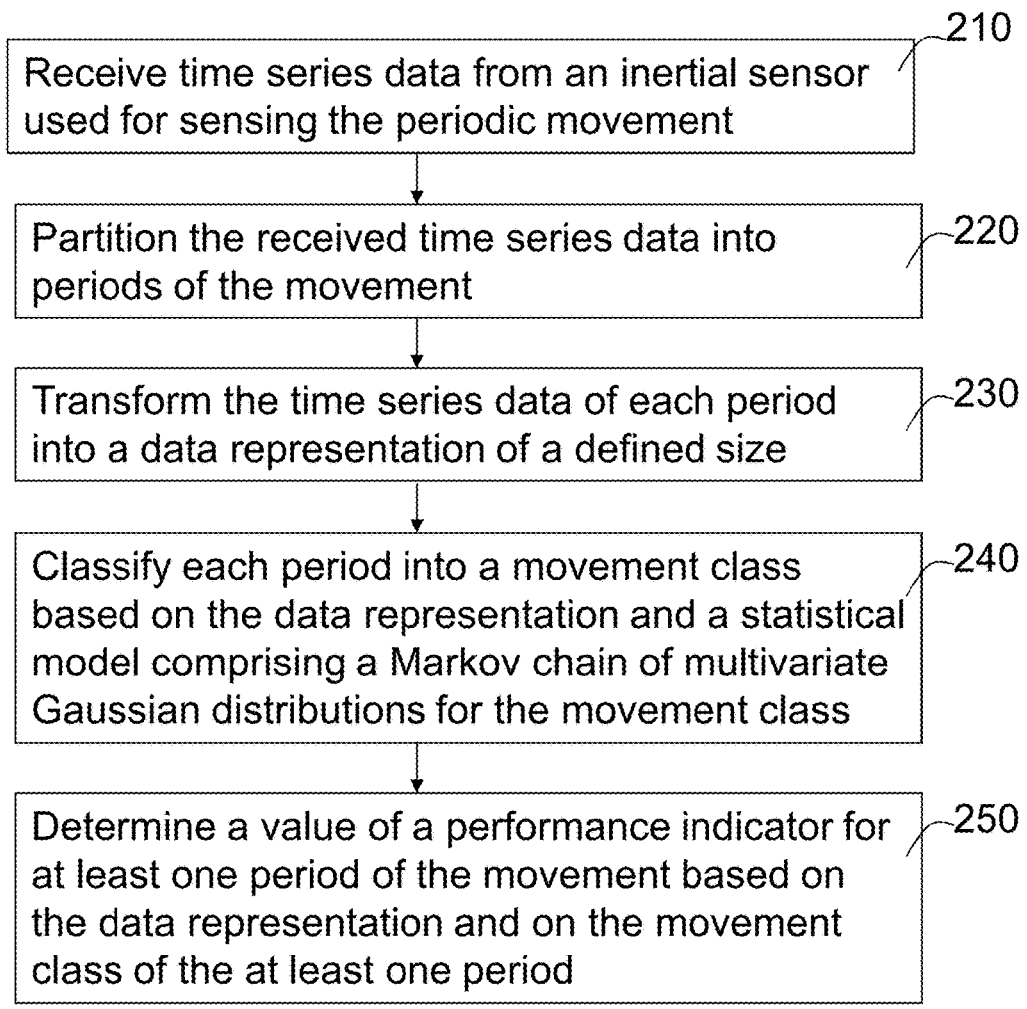
FIGS. 2*a-b* are flowcharts illustrating the method according to embodiments.

FIG. 2a is a flowchart illustrating the method for determining a value of a performance indicator for a periodic movement performed by a human or an animal according to an embodiment of the invention. In one embodiment, the periodic movement is a movement of a cross-country skiing person. The method comprises:

- 210: Receiving time series data from an inertial sensor used for sensing the periodic movement. The sensor may be an accelerometer or a gyroscope. An accelerometer may provide data from the sensed movement in different directions or axes. A three-dimensional accelerometer would e.g. provide data in three perpendicular directions: The lateral movement direction, the vertical movement direction, and the horizontal backward and forward movement direction. The received time series data is thus three-dimensional, and may provide support for a rather detailed movement analysis. However, a one dimensional accelerometer may be enough for the purpose of the invention, depending on the type of periodic movement that is to be analyzed. If the movement is primarily in the vertical direction, a one-dimensional accelerometer may be enough for a good analysis. In the following, the sensor used is assumed to be a three-dimensional accelerometer. Furthermore, the sampling rate of the sensor has to be high enough to allow for a useful analysis. In one example embodiment suitable for the analysis of a ski skating movement, the sampling rate is in the order of one sample every 10 ms.
- 220: Partitioning the received time series data into periods of the movement or into partitions of the movement each corresponding to a period of the movement. The purpose of the partitioning is thus to get a data representation of the sensor data for each period of the movement, such that each movement period may be analyzed. For ski-skating, a period is typically of the length of 0.8-1.6 seconds. The partitioning may in embodiments comprise low-pass filtering the received time series data to identify limits between each period of the movement. By low-pass filtering the data received with a low cut-off frequency, the periods of the movement will stand out clearer from the filtered data. This allows to pin-point when in time one movement period stops and the next one begins based on the data. In alternative example embodiments, the limits between the periods may be identified as the point in time when the filtered data has a peak, or when it passes zero in one direction (upward or downwards). In the example of ski skating, a period is typically of a length of 0.8-1.6 seconds as already mentioned above, and a low enough cut-off frequency for the low-pass filtering may then be 1-2 Hz. The partitioning of the time series data may then be done in accordance with the identified limits. As the limits between the periods have been identified, the received sensor data may be cut up or partitioned into periods accordingly.
- 230: Transforming the time series data of each period into a data representation of a defined size. This step is together with the partitioning of the data into periods also referred to as the pre-processing of the sensor data, crucial for the possibility to do a classification and to determine performance indicator values based on the data representation. Furthermore, the pre-processing may be performed in real-time based on streaming data. The transforming may in embodiments comprise a low-pass filtering of the time series data of each period to reduce noise. In this way the trajectory of the movement will be accentuated, and only relevant information is kept. Typically a higher cut-off frequency is used than when identifying the periods. In the example of ski skating with periods slower than 1 Hz, a suitable cut-off frequency for the low-pass filtering might be around 5 Hz. The transforming may then also comprise a re-sampling of the low-pass filtered data to form a data representation of a defined size. As a time period of the skiers movement is not constant, due to variations in the skier's performance e.g. because of the steepness of a ski track slope, the data corresponding to a period needs to be re-sampled in order to get a data representation of a defined size. Another reason for the re-sampling is that the sensor's sampling rate may present a variation over time such that the time between samples may be slightly differing. There are several alternative embodiments possible for the transformation into a data representation of a defined size. Alternatives may be to use a Fourier transform method or a Principal Component Analysis (PCA) method.

240: Classifying each period into a movement class based on the data representations and a statistical model comprising a Markov chain of multivariate Gaussian distributions for each at least one movement class. If only one movement class is modeled, a statistical anomaly detection method can be used to determine whether a movement period belongs to that class. With one movement class for each type of movement, a statistical machine learning method can be used to classify the movement period.

250: Determining a value of a performance indicator for at least one period of the movement, based on the data representations and on the movement class of the at least one period. Values of several different performance indicators may be determined for one or several periods of the movement. For some performance indicators, information related to the classification of a period may not always be needed.

In the following, different embodiments related to the determining of values of different performance indicators are described. As explained above, the data representations may consist of low-pass filtered three-dimensional accelerometer time series data which is resampled such that each period is represented by the acceleration at a defined number of steps, the so called data representation. The data representation of a period may also be referred to as a vector for the period, or simply a period vector, where each vector element corresponds to an acceleration value. Each step or each vector element thus represents the acceleration at a fixed phase of the movement. Values of different types of performance indicators may therefore be deduced directly from the data representations. This makes the process for determining performance indicators for a period of the movement simple and fast as the determining requires no more input than the pre-processed time-series data or the data representation of the period, and optionally also information related to the movement class to which the data representation of the period corresponds.

A performance indicator that may be interesting for any periodic movement and movement class is a level of consistency between several periods of a same movement class. The level of consistency is inversely related to the variance of the pre-processed time series data, also referred to as the data representation, for a number of periods N. The level of consistency is thus high if the variance is low and vice versa. However, the level of consistency must also be put in relation to the total variance of acceleration within the periods, to avoid that small movements appear more consistent than large ones just because of their lower total variance. Explained with reference to a more detailed example, a phase dependent variance $V_{PHASE}$ may be defined as the average of the square distances between each of the period vectors to an average vector of all N period vectors. If the total acceleration variance $V_{TOTAL}$ is defined as the average of the variances in acceleration values in each of the three directions, the value of the level of consistency may e.g. be calculated as the square root of $(V_{TOTAL}-V_{PHASE})/V_{TOTAL}$. This measure is 1 when the vectors of the N periods are all equal and close to 0 when they are completely unrelated to each other. The value of the level of consistency thus indicates if the human or animal performs the periodic movement in a consistent manner or not. An advantage of determining the value of the level of consistency in this way is that it may be done in real time as it may be deduced directly from the data representations.

Alternatively, a similar scheme can be used to compare a movement period with a reference movement for the same movement class instead of with the same person's movement. The reference movement may be from an ideal reference, or it may simply be another person's movement. In this case, when calculating $V_{PHASE}$, the square distance between one or several movement period vectors to the reference movement period vector is used instead of to the average of those one or several movement period vectors. In such a case the value of level of consistency gives an indication of similarities and differences between e.g. two persons performing a same movement. Such a performance indicator may be interesting e.g. when comparing performance and techniques of the two persons, and when analyzing a connection between the movement and different kinds of injuries. Both consistency relative a reference movement and consistency relative the athletes own movement may thus be assessed using the consistency level performance indicator.

In one embodiment, the performance indicator may comprise a level of consistency for at least two periods classified into a same movement class. The value of the level of consistency may be determined based on a variance of the data representation for the at least two periods.

A further performance indicator may be a frequency of movement. For a cross country skier using a skate technique it may for example be interesting to know the frequency of the movement e.g. when using gear 3. For this performance indicator a plurality of subsequent periods of the same movement class corresponding e.g. to gear 3 are analyzed with regards to how many periods that occur during the time lapsed during all of the subsequent periods. This gives a value for the frequency of movement classified as gear 3.

Thus, in a further embodiment, the performance indicator may comprise a frequency of movement. The value of the frequency of movement may be determined by dividing an amount of subsequent periods classified into a same movement class with the time lapsed during said subsequent periods.

Still another performance indicator that may be interesting for e.g. a runner is a level of symmetry for one period of the movement. One period of a runners periodic movement e.g. classified into the movement class of heel-toes running, may be determined to start when the heel of the right foot comes in contact with the ground and to stop right before the heel of the right foot comes into contact with the ground next time. A second half of the period starts when the runner's heel of the left foot comes into contact with the ground. Ideally, the first and the second half of the movement period should be symmetric, so a level of symmetry value could be a valuable performance indicator. To calculate the symmetry it is noted that the data representation of a perfectly left-right symmetric movement should look similar to itself if phase-shifted half a period and mirrored along the x-axis. $V_{MIRROR}$ may thus in one embodiment be defined as the square distance between a period vector and the same period vector phase shifted and with changed sign on all acceleration values in the x-direction. $V_{TOTAL}$ is again the total acceleration variance of the period. The symmetry may then be calculated e.g. as the square root of $(V_{TOTAL}-V_{MIRROR})/V_{TOTAL}$.

In another embodiment, the performance indicator comprises a level of symmetry for a period classified into a movement class corresponding to a symmetric movement, such as a runner's periodic movement. In this embodiment, the value of the level of symmetry is determined based on a variance of the data representation of the period and a cyclically phase-shifted and mirrored data representation of the period.

Figure 6:
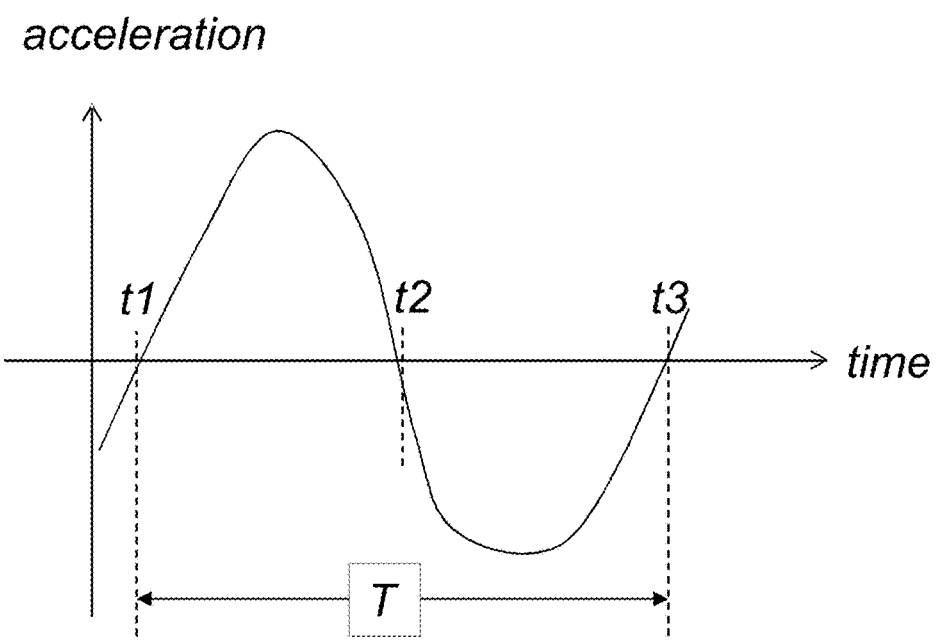
FIG. 6 is a graph schematically illustrating forward acceleration value as a function of time.

A performance indicator that may be interesting for the movement class of double poling for a cross-country skier using a classic technique is a propulsion indicator. When looking at the periodic movement of a skier that is classified into the double poling movement class, it is interesting to know how much of the movement period that corresponds to the pushing on the poles, which is the part of the periodic movement that contributes to the propulsion of the skier in the direction of movement of the skier. The purpose of the propulsion indicator is to provide a measurement of this contribution to the propulsion of the skier. The time of the period that the poles are in the snow and are used to push the skier forward is put in relation to the time of the total period, which thus gives a measure of how much of the movement period that is used for propulsion of the skier forward. This is illustrated in the graph in FIG. 6, illustrating a forward acceleration value as a function of time. The forward acceleration over time is taken directly from the pre-processed data representation. One period of the movement corresponding to the movement class of double poling is illustrated. T=t3−t1 is the total period time. Between time t1 and time t2, the forward acceleration values are positive and correspond to the time of the period when the skier is pushed forward, i.e. the time of propulsion. From time t2 until the end of the period at t3 the acceleration values are negative and the time period thus corresponds to the time of retardation when the poles are not contributing to the forward movement. The propulsion indicator is calculated as (t2−t1)/T. Based on the data representation, the length of the longest sequence of positive forward acceleration values may be determined and may be divided by the total length of the period to get the propulsion indicator.

The propulsion indicator may also be interesting for a runner. In a movement period for a runner it is possible to determine from the period vector during what time the runner has contact between foot and ground, sometimes referred to as a contact time. The contact time for both the right and the left foot during a movement period is put into relation to the time of the total movement period, thus determining a value for the propulsion indicator for the runner. In the example of a sprinter, the contact time is preferably short in order for the sprinter to run fast, and the performance indicator should thus have a low value for a well performing sprinter.

Thus, in one embodiment, the performance indicator may comprise a propulsion indicator for a period. Determining 250 the value of the propulsion indicator may comprise determining a first time value corresponding to a sequence of positive forward acceleration values in the data representation of the period, determining a second time value corresponding to the time of the period, and dividing the first time value with the second time value.

Another example of a performance indicator may be a force indicator, e.g. for a cross-country skier. The value of the force indicator may be determined by multiplying the weight of the skier with the acceleration of the skier in the direction of movement. Furthermore, a power indicator may be determined as the force indicator value multiplied by the skiers speed. To determine a force indicator, information related to the speed of the skier is required. The speed is not directly retrievable from the pre-processed time series data from the inertial sensor and must therefore be retrieved from e.g. a GPS receiver carried by the skier. In the case of the force indicator, the weight of the skier is needed. Such personal data may e.g. be entered manually into the system by the skier. Therefore, additional information such as pulse beat information or positioning information may be retrieved from other sensors and devices, or may be entered e.g. via a user interface, to make it possible to determine diverse performance indicators.

In embodiments of the invention that may be combined with any of the above described embodiments, the method may comprise also the building up of the statistical model used for the classification of the movement based on the data representation derived from pre-collected time series data associated with at least one movement class. By pre-collecting time series data from e.g. skier's when they are performing a certain type of skating technique, the model may be built up in beforehand. In one embodiment, wherein the pre-processing and the classification is performed in the unit 100 carried by the skier, the model may be downloaded from a server 110 in order to perform the classification. However, another possible embodiment is that the statistical model is built up based on the skier's own movements. It may be enough to build the model on only ten periods from a periodic movement of a certain movement class. The model may then be used in the unit 100 for further analysis of the skier's movements. In this scenario, the step of building up the model may be performed after the step 210 of receiving time series data from the sensor. The pre-processing of the sensor data is thus also useful for the build-up of a powerful statistical model.

Embodiments of the method may also comprise the storing of at least one of the received time series data, the data representation, information related to the classification of the periodic movement, and the performance indicator values. Typically, the storing will be done in a database 120 connected to a server 110. By storing the raw data, any analysis is possible to perform in the future. However, storing only the pre-processed data representation diminishes the requirement on storing capacity. It may also be interesting to store the classification results for a certain skier and the performance indicators, as well as e.g. information related to what ski track the information corresponds to. The stored performance indicators may e.g. be used to compare different skiers or a same skier over time.

As already described above, the statistical model used for the classification comprises a Markov chain of multivariate Gaussian distributions for the movement class. In more detail this means that the probability distribution over the data representation X of a movement period, consisting of k*n elements where k is the number of sensors and n the number of time steps in each period after the transformation, comprising e.g. the filtering and the re-sampling, is for each movement class C modeled as:

$$P(X \mid C) = P(\acute{x}_0 \mid C) \prod_{i=1}^{n} P(\acute{x}_i \mid \acute{x}_{i-1}, C) \quad [1]$$

where each $\acute{x}_i$ contains the k sensor values corresponding to the i:th time step, and each factor $P(\acute{x}_i \mid \acute{x}_{i-1}, C)$ is represented by a 2*k dimensional multivariate Gaussian distribution.

The parameters of the Gaussian distributions are estimated from previously collected sensor data from each movement class.

When the statistical model comprising more than one movement class is used for classification, Bayes theorem may be used to calculate the probability that a data representation X of a movement period belongs to a certain movement class C. The probability is calculated for each movement class C using:

$$P(C|X) \propto P(X|C)P(C) \quad [2]$$

where P(C) is the prior probability of each class which is typically assumed to be the same for all classes, and ∝ stands for "is proportional to". The movement class with the highest probability is then selected.

When the statistical model comprises only one class, the data representation X of the movement period is said to belong to the class of the model when:

$$P(X|C) > \varepsilon \quad [3]$$

where ε is a suitably selected threshold.

An advantage of using a statistical model comprising a Markov chain of multivariate Gaussian distributions is that the model is robust, as the Markov chain allows to break up the very high dimensional input space into a number of smaller dimensional input spaces, and each Gaussian distribution is not as sensitive to noise and deviating values as a more complex non-linear model may be. Furthermore, the build-up of the model, as well as the classification based on the model, is computationally efficient. This means that it is possible to classify data from a three-dimensional accelerometer and determine performance indicators based on the data and the classification without problems with regards to computation performance.

Figure 2B:
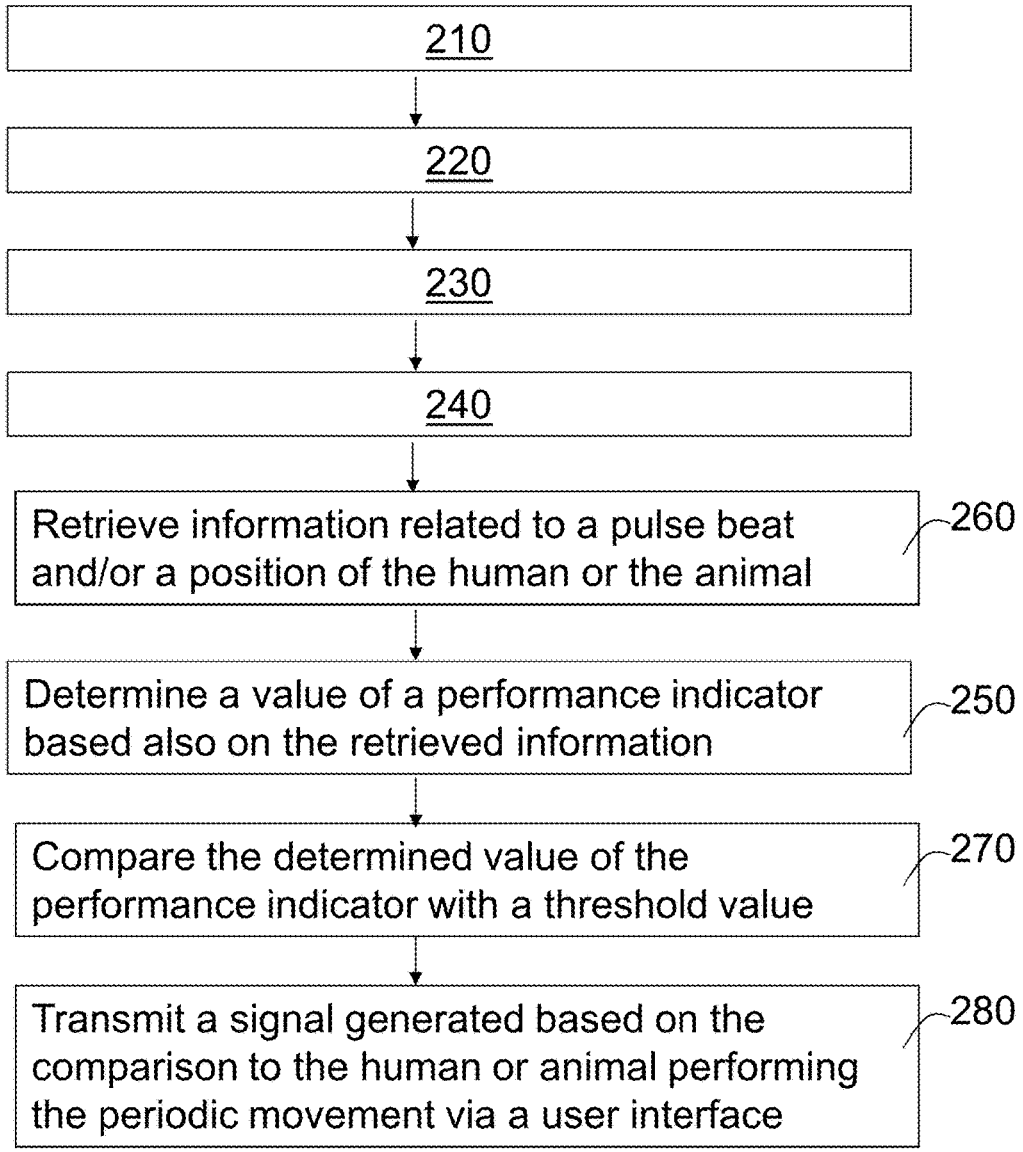

FIG. 2b is a flowchart illustrating the method for determining a value of a performance indicator for a periodic movement performed by a human or an animal according to a further embodiment of the invention. The method according to any of the embodiments described above may optionally comprise, in addition to e.g. the steps described with reference to FIG. 2a, at least one of:

- 260: Retrieving information related to at least one of a pulse beat and a position of the human or the animal when performing the periodic movement. The value of the performance indicator may then be determined based also on the retrieved information.
- 270: Comparing the determined value of the performance indicator with a threshold value.
- 280: Transmitting a signal generated based on the comparison to the human or animal performing the periodic movement via a user interface. The signal may be at least one of an audio signal, a tactile signal, and a visual signal. As described above, the audio or tactile signal may be more convenient for the athlete during the exercise. Visualizing the feedback in a user interface is probably more useful e.g. for a trainer following the skier's performance. The trainer may want to visualize the performance indicator results or the feedback signals. The result from the classification and the performance indicators may e.g. be visualized in a graphical web user interface. External analysis programs such as Excel or Mathlab may also be used to view the results.

Figure 4A:
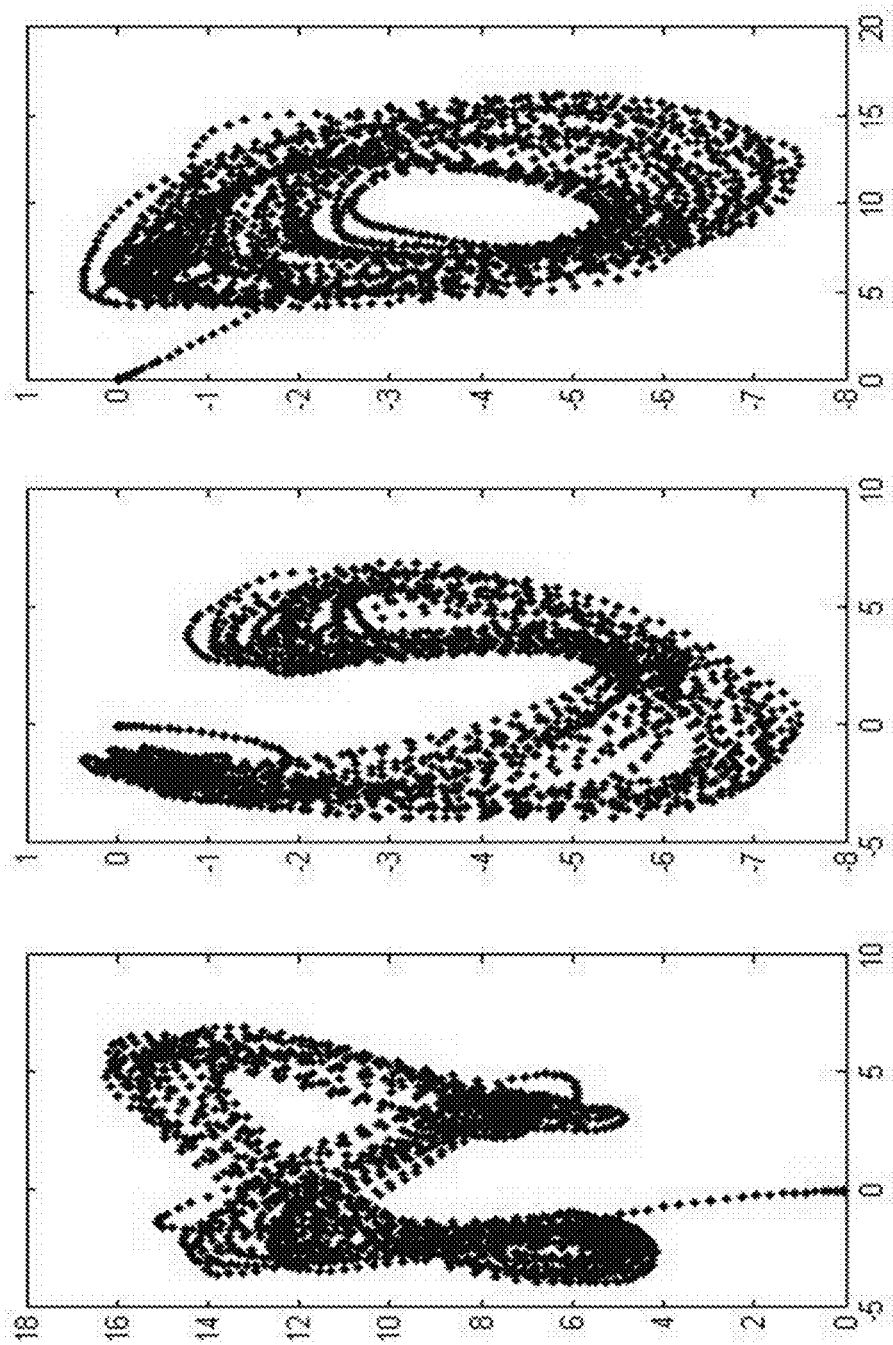
FIGS. 4*a-c* are plot diagrams of raw data collected from three different skiers using skating gear 2.
Figure 4B:
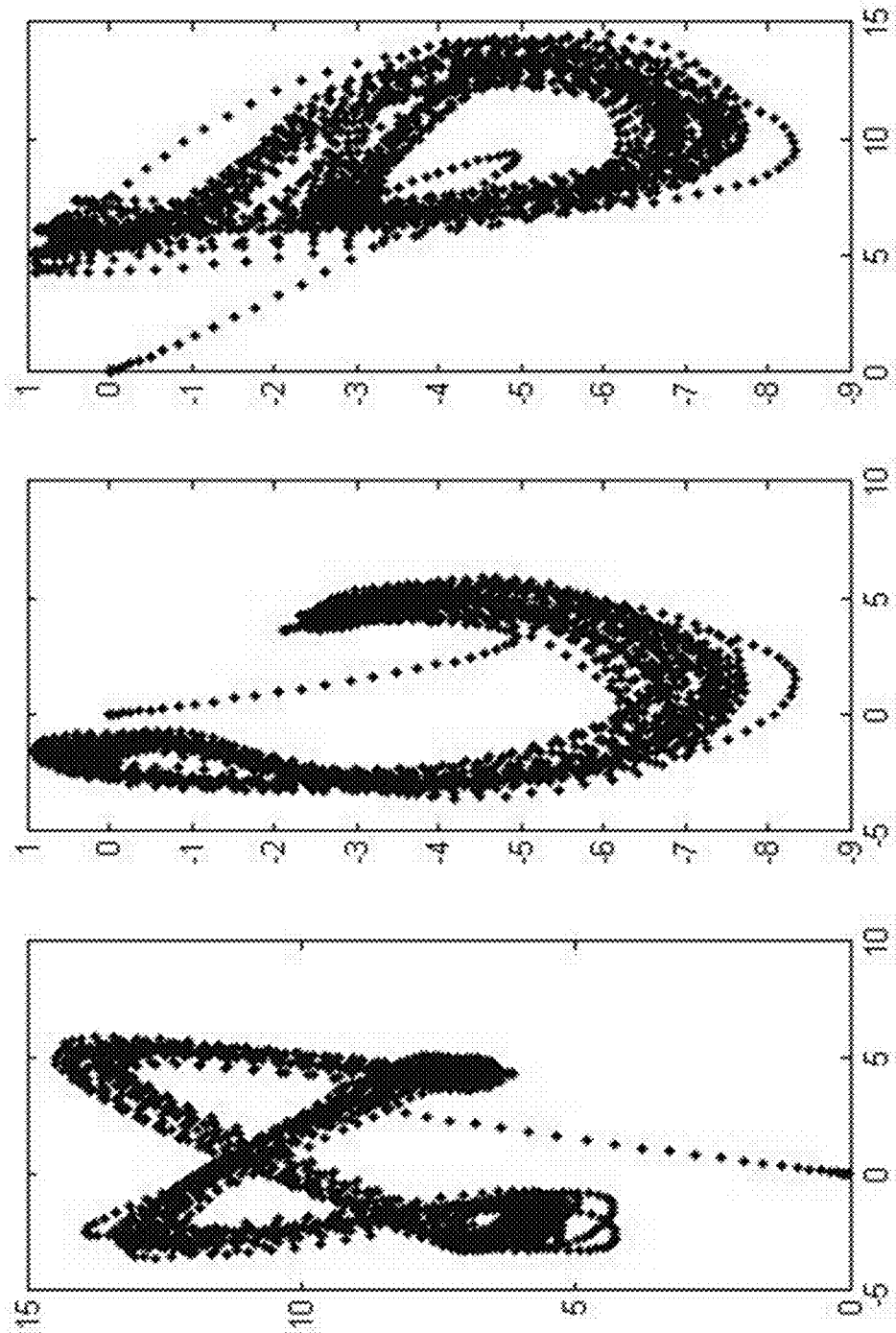
Figure 4C:
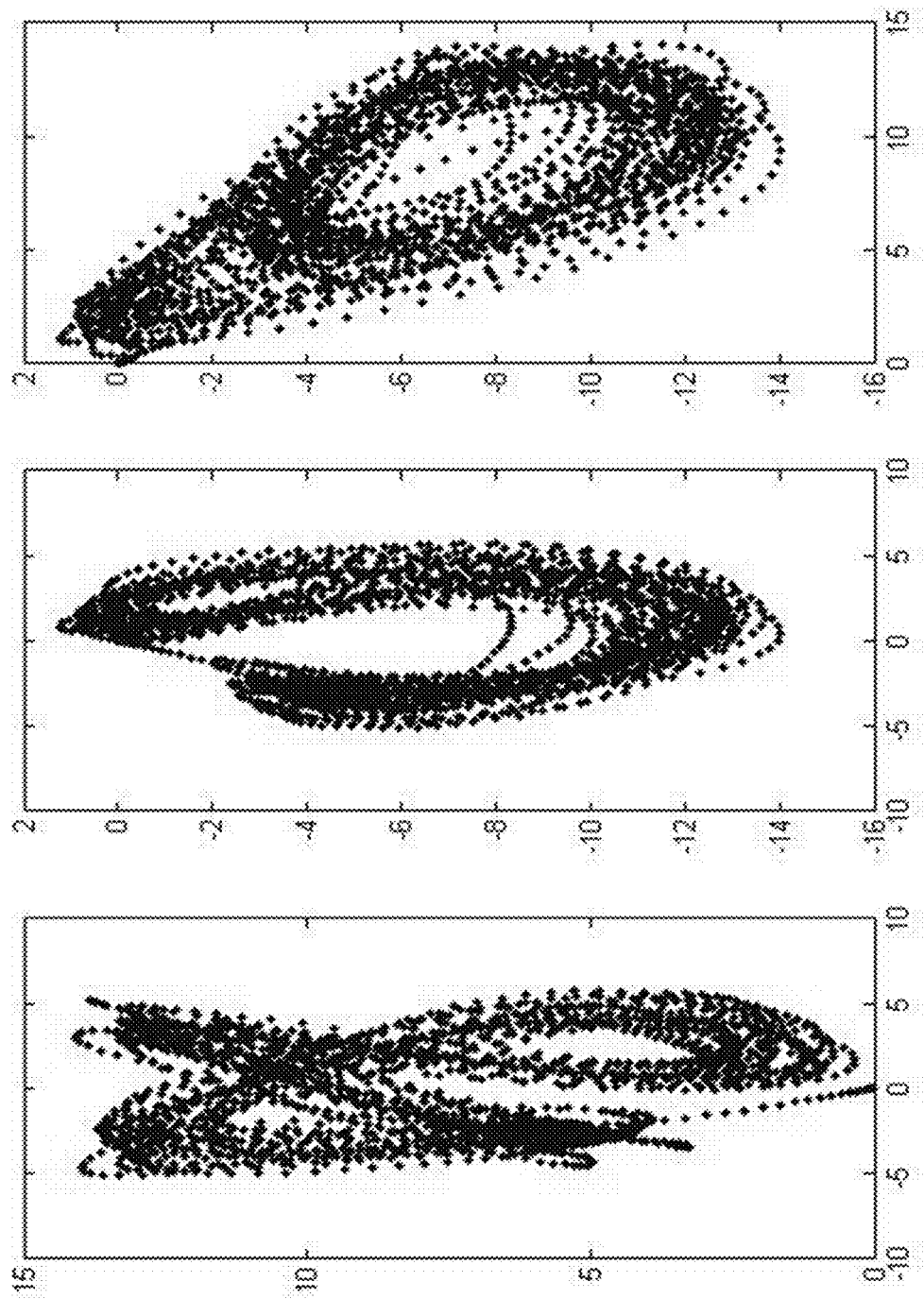
Figure 5A:
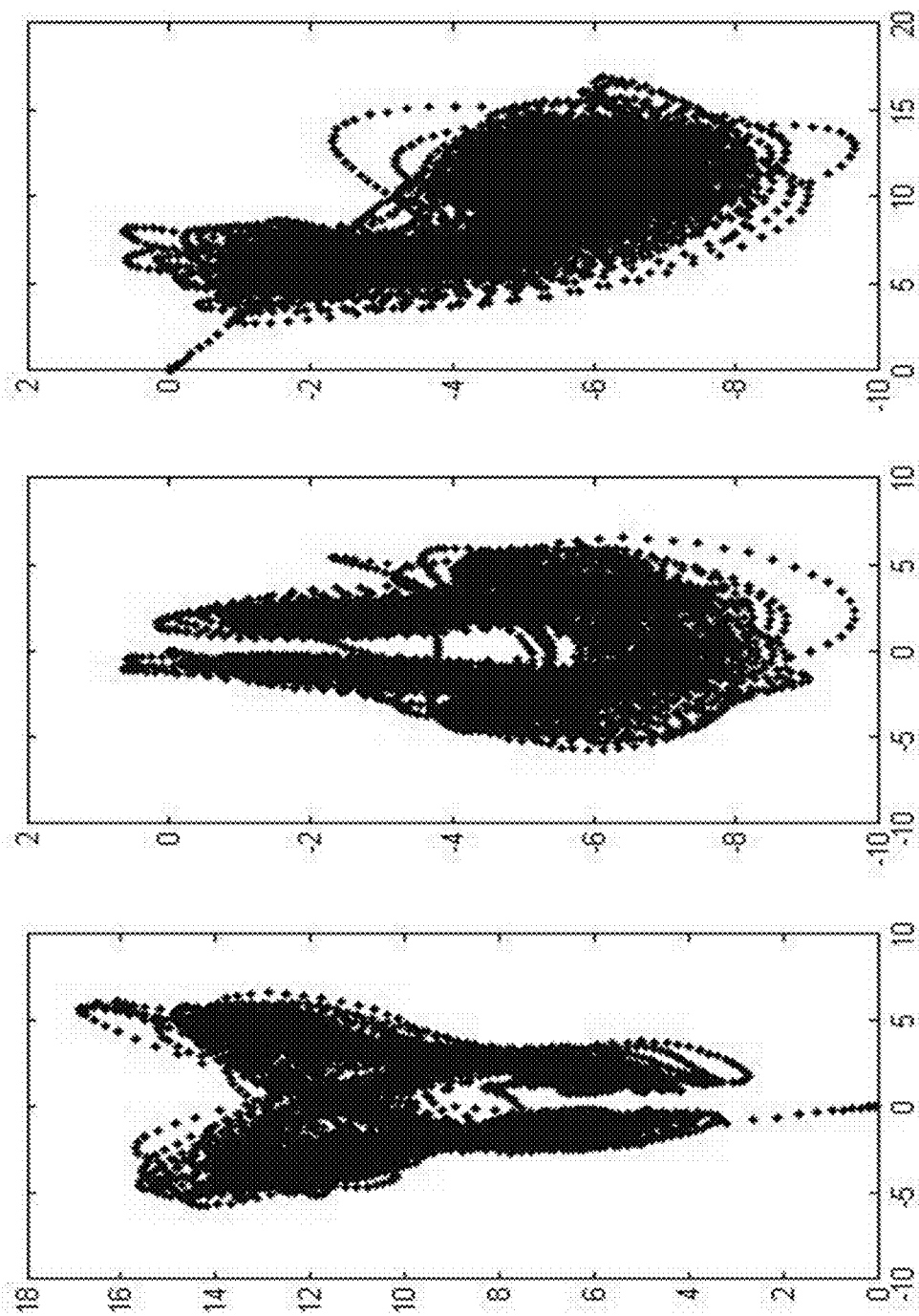
FIGS. 5*a-c* are plot diagrams of raw data collected from three different skiers using skating gear 3.
Figure 5B:
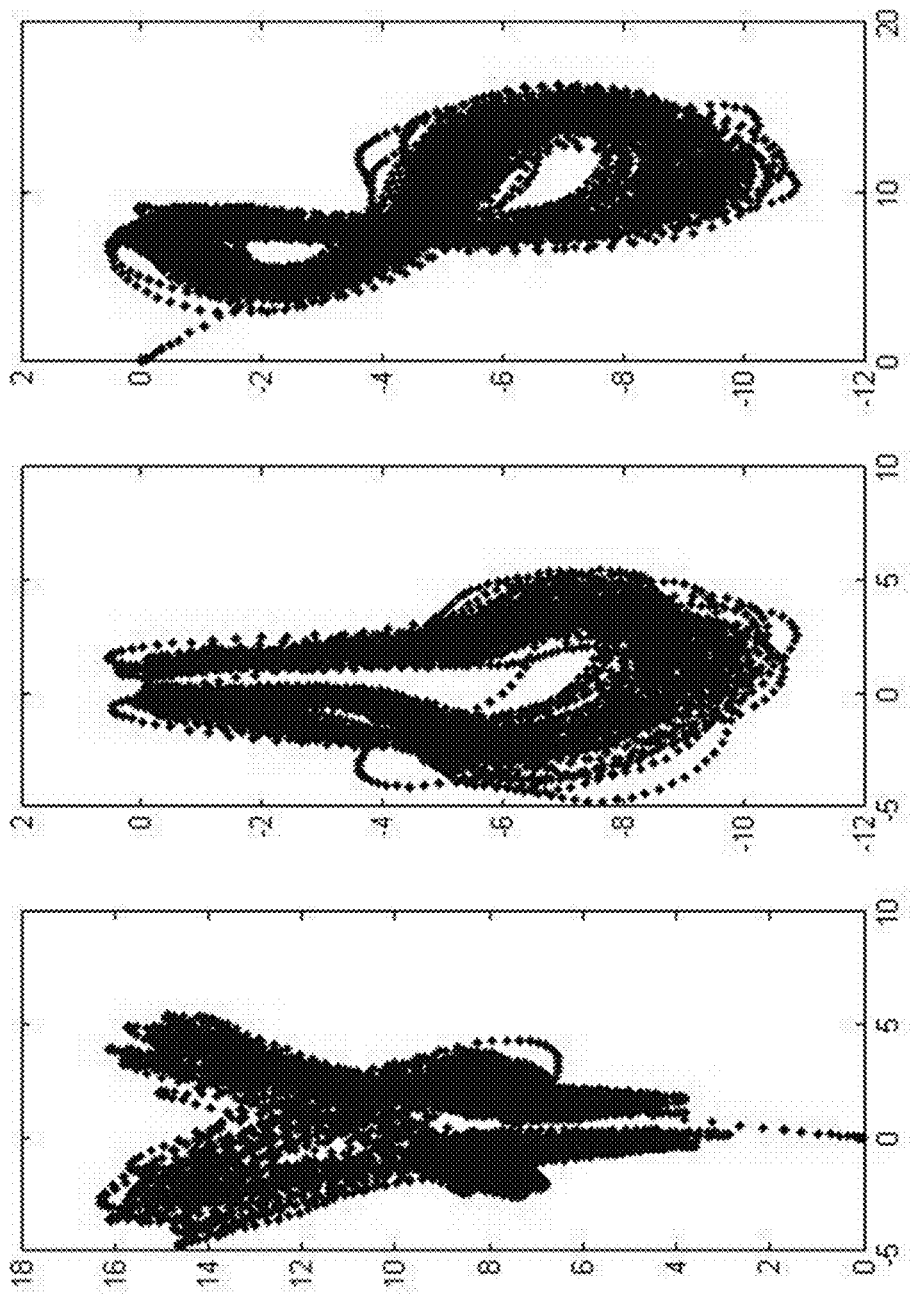
Figure 5C:
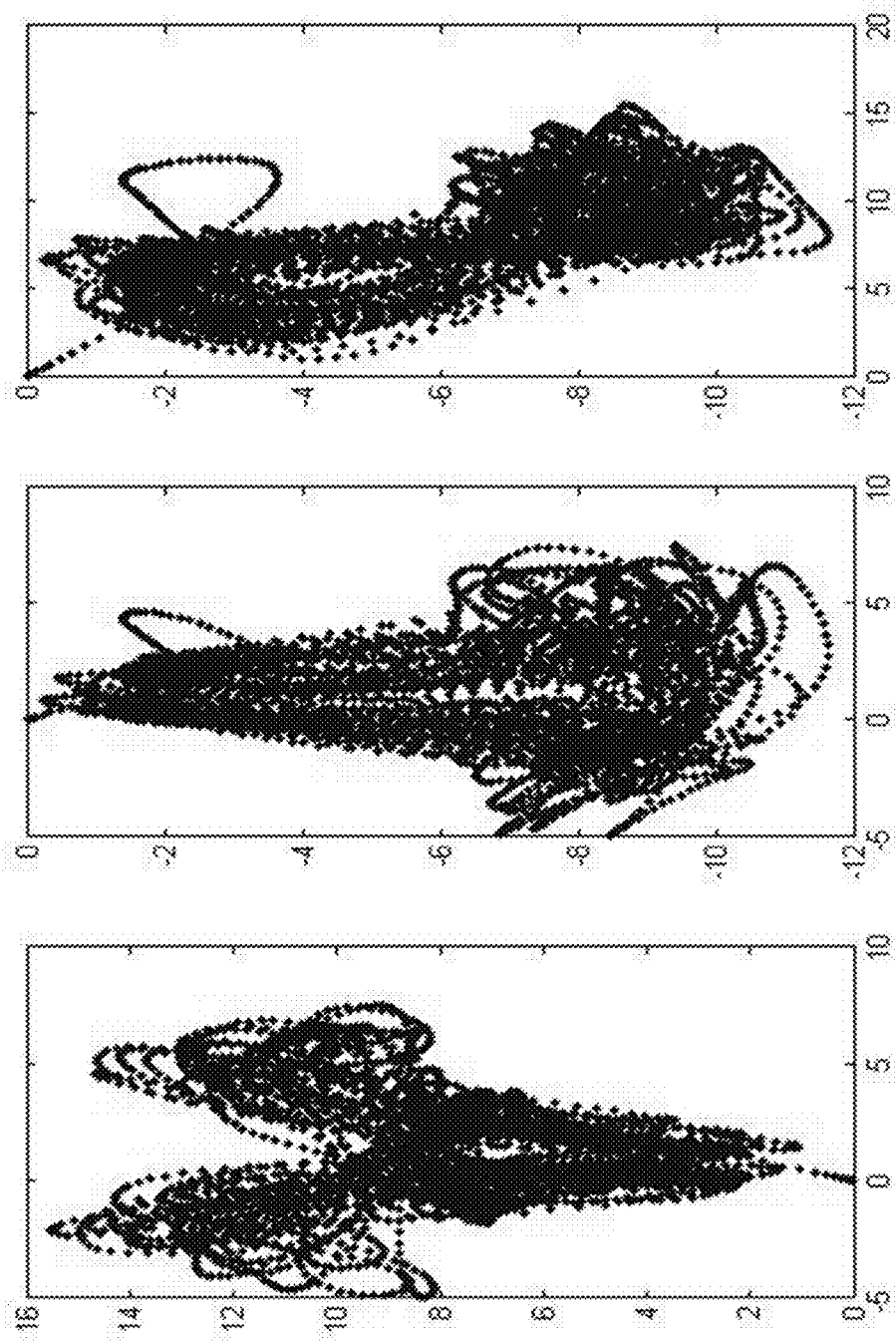

FIGS. 4a-c and FIGS. 5a-c illustrate plot diagrams produced from raw data received from a three-dimensional accelerometer fixed on the chest of skiers performing the periodical movement of a defined ski skating gear. FIGS. 4a-c illustrate the plot diagrams for three different skiers (one skier per figure) using skating gear 2, and FIGS. 5a-c illustrate the plot diagrams for the three different skiers using skating gear 3. In each figure, the left most plot diagram shows the acceleration of the lateral movement on the x-axis of the diagram, and the acceleration of the vertical movement on the y-axis of the diagram. The middle plot shows the acceleration of the lateral movement on the x-axis, and the acceleration of the horizontal backward and forward movement on the y-axis. The right most plot diagram shows the acceleration of the vertical movement on the x-axis, and the acceleration of the horizontal movement on the y-axis. Said movement directions, i.e. the lateral, the vertical, and the horizontal movement directions are perpendicular to each other.

In one use case of the present invention, the skier wants to receive performance indicator information during an exercise. The performance indicator values should also be stored together with the used skating class at given times during an exercise. The skier fastens the unit 100 on her chest with an elastic ribbon, which may e.g. be a smart phone comprising an accelerometer, and an application adapted to receive the sensor data and to perform the pre-processing, the classification and the determining of the performance indicator values. The application is started and the skier carries out the skating exercise in the track. During the exercise, sound and/or tactile signals are fed back to the skier via a sound/tactile user interface 104, thus indicating how the skier is performing. The feedback signals are generated based on a comparison of the continuously determined performance indicator values with threshold values. When the exercise is finished, the results may also be viewed on the smart phones display, e.g. in a graphical view. Furthermore, the results may be viewed by the skier's trainer by accessing the result via the internet server. More detailed analysis may also be performed on the server, either in real-time, or at a later stage.

Another example scenario, in which embodiments of the invention may be applied, is the evaluation of the periodic movement of a hockey player that e.g. performs repetitive exercises during a training session, thus producing a periodic movement. A training session could e.g. comprise evaluation of the stick handling during dribbling. A period of movement for a dribble may be defined as the movement of bringing the stick back and forth once to hit the puck. Interesting performance indicators may be the amount of dribbles performed during a certain time interval, i.e. a calculation of the frequency of movement, as well as the consistency of the movement measured over more than one period. Another movement example may be wrist shots performed by a hockey player during a training session, where one period of the movement corresponds to one wrist shot. The frequency as well as the consistency of the movement may be interesting performance indicators to evaluate also this movement. A further movement example may be a vertical jump of the hockey player on ice skates, where the performance indicators may be needed to measure and evaluate the strength of the hockey player's legs looking at the time in the air and the height over ice.

Also the actual skating stride technique of the hockey player may be evaluated for investigating e.g. her speed and agility in skating. The periodic movement of a hockey player performing different skating strides may be analyzed and evaluated. Each period of the movement may e.g. be classified in different movement classes of e.g. forward skating stride, backward skating stride, forward cross-over, and backward cross-over. Different performance indicators such as those described previously and used for cross-country skiers or runners may be determined and used also for evaluating a hockey players skating stride technique.

Figure 3A:
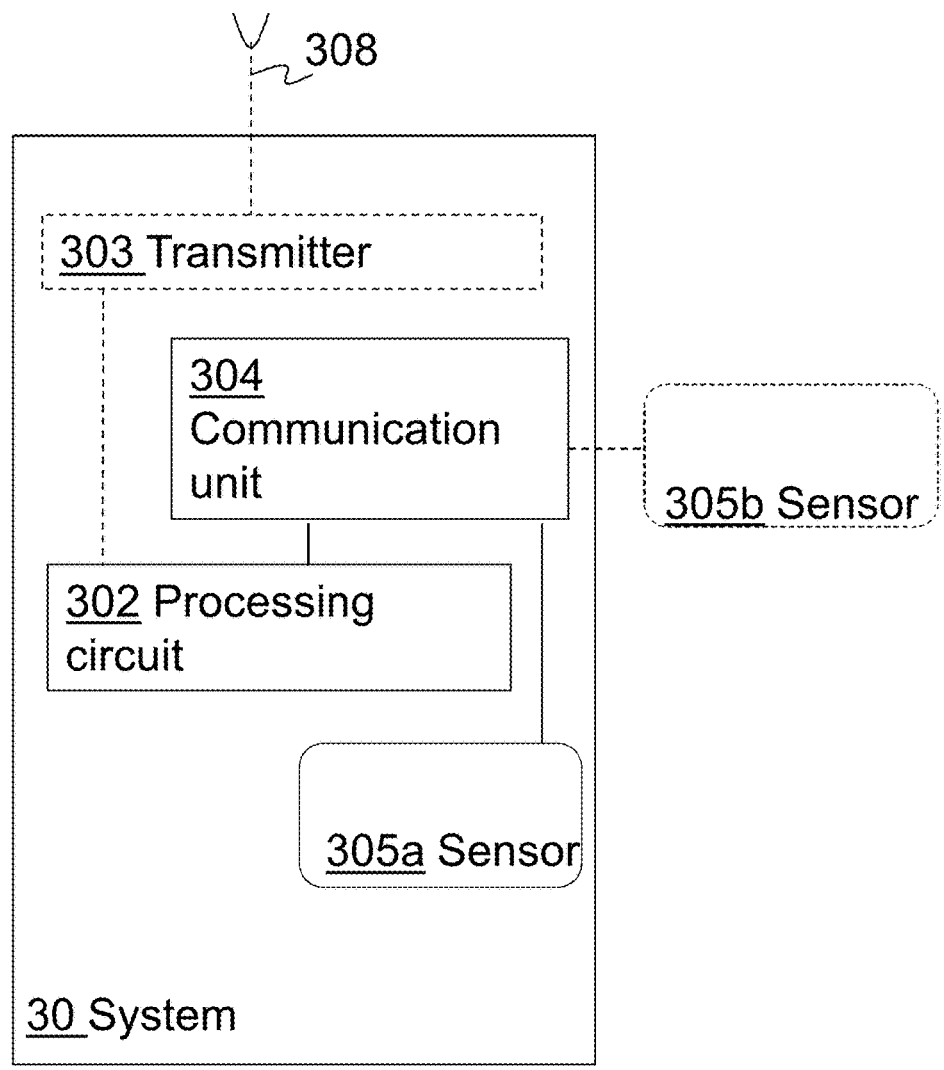
FIGS. 3*a-b* are block diagrams schematically illustrating the system according to embodiments.

An embodiment of a system 30 for determining a value of a performance indicator for a periodic movement performed by a human or an animal is schematically illustrated in the block diagram in FIG. 3a. The system 30 comprises an inertial sensor 305a for sensing the periodic movement. The sensor may be an accelerometer and/or a gyroscope. The system also comprises a communication unit 304 connected to a processing circuit 302. The communication unit 304 is configured to receive time series data from the inertial sensor 305a. The processing circuit 302 is configured to partition the received time series data into periods of the movement, and transform the time series data of each period into a data representation of a defined size. The processing circuit 302 is also configured to classify each period into a movement class based on the data representations and a statistical model comprising a Markov chain of multivariate Gaussian distributions for each at least one movement class. The processing circuit 302 is further configured to determine a performance indicator for at least one period of the movement, based on the data representation of at least one period, and on the movement class of the at least one period. The performance indicator may comprise one or more of the above described performance indicators, and the processing circuit 302 may be configured to determine the performance indicators according to any of the embodiments described above with reference to the method.

The system may in this embodiment correspond to the unit 100 in FIG. 1 that the skier is carrying. The communication unit 304 may optionally be configured to receive data from an additional sensor node 305b, or from another device. The additional sensor node may be a pulse beat sensor for sensing pulse beats of the human or the animal when performing the periodic movement. An example of other devices that may be connected is a GPS receiver device. Such additional sensors or devices may be used for determining a position or a speed of the human or the animal when performing the periodic movement and the processing circuit 302 may be configured to determine the value of the performance indicator based also on the retrieved information. The system may optionally comprise a transmitter 303 connected to one or more antennas 308 for transmitting sensor data or analysis results to e.g. an external server. The system may in embodiments also comprise a receiver for receiving data from the external server e.g. via the one or more antennas 308.

In an alternative way to describe the embodiment in FIG. 3a, the system 30 comprises a Central Processing Unit (CPU) which may be a single unit or a plurality of units. Furthermore, the system comprises at least one computer program product (CPP) in the form of a non-volatile memory, e.g. an EEPROM (Electrically Erasable Programmable Read-Only Memory), a flash memory or a disk drive. The CPP comprises a computer program, which comprises code means which when run on the system 30 causes the CPU to perform steps of the procedure described earlier in conjunction with FIG. 2a. In other words, when said code means are run on the CPU, they correspond to the processing circuit 302 of FIG. 3a.

Figure 3B:
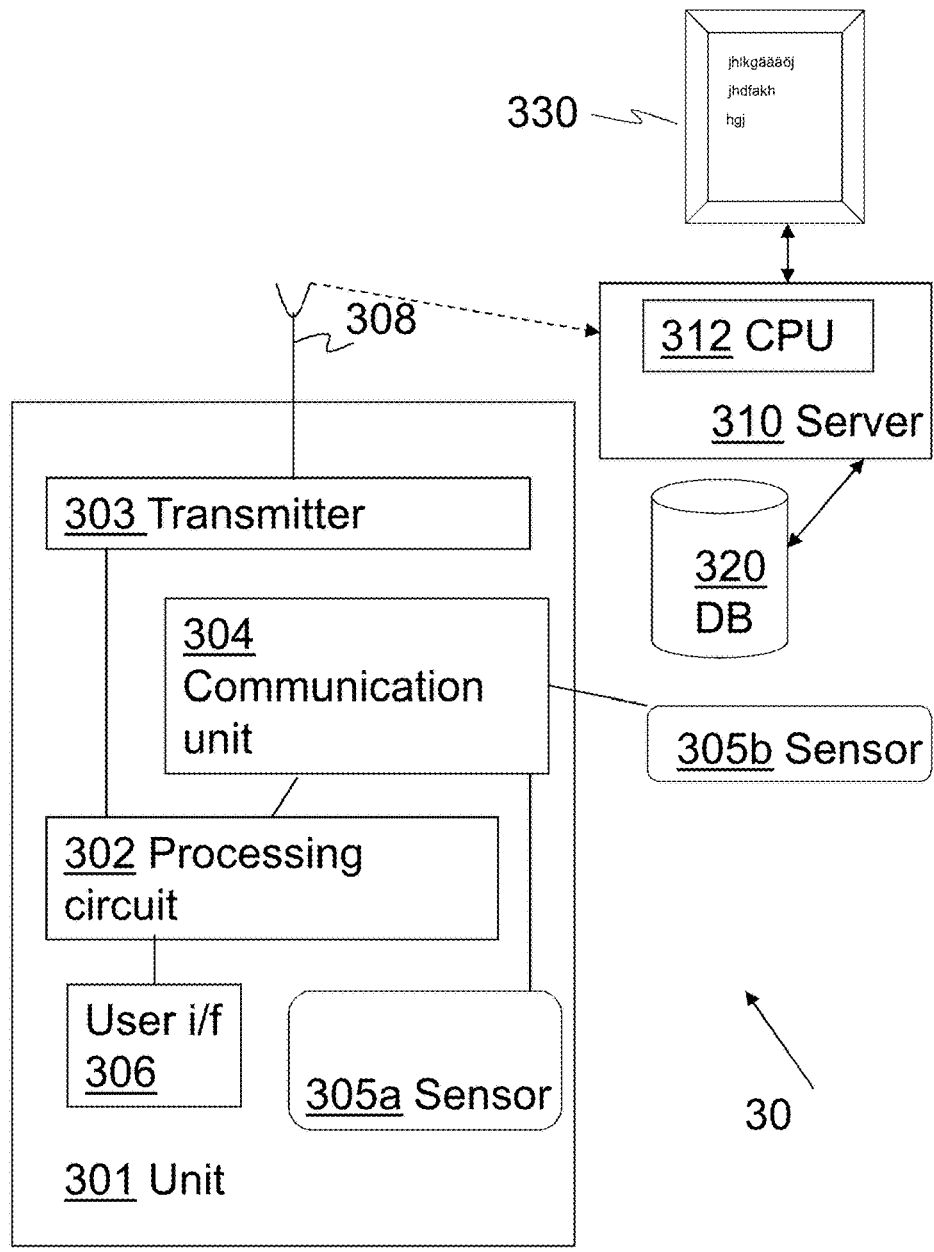

Another embodiment of the system 30 is schematically illustrated in the block diagram in FIG. 3b. The system may in this embodiment correspond to the whole of system 10 in FIG. 1. The system 30 comprises an inertial sensor 305a for sensing the periodic movement, comprised in the unit 301 carried by the skier performing the periodic movement. The unit 301 also comprises a communication unit 304 connected to a processing circuit 302. The communication unit 304 is configured to receive time series data from the inertial sensor 305a, and possibly from an additional sensor node 305b. The system 30 further comprises a server 310, and the unit 301 comprises a transmitter 303 connected to an antenna 308 for transmitting sensor data, data representations, classification results, and/or performance indicator values to the server 310, e.g. via a mobile network. The system may in embodiments also comprise a receiver for receiving data, such as the downloaded statistical model from the external server. The received sensor data may in one embodiment be transmitted to the server 310, and a processing circuit 312 on the server 310 is configured to partition the received time series data into periods of the movement, transform the time series data of each period into a data representation of a defined size, classify each period into a movement class based on the data representations and the statistical model, and determine a performance indicator for at least one period of the movement, based on the data representation and on the movement class of the at least one period. However, as already described previously, in an alternative embodiment, the pre-processing of the sensor data may be performed by the processing circuit 302 in the unit 301, and the pre-processed data may be transmitted to the server 310 for classification and for determining performance indicator values. The system is in embodiments further adapted to store at least one of the received time series data, the data representation, information related to the classification of the periodic movement, and performance indicators. The system 30 may thus further comprise a database 320 connected to the server 310, adapted to store sensor data, classification results, or performance indicators. The database 320 may in embodiments be integrated with the server 310. The system may be further adapted to build up the statistical model based on the data representation derived from pre-collected time series data associated with the at least one movement class.

In a further embodiment, the system 30 may further comprise a user interface 306. The processing circuit 302 may be further configured to compare the determined value of the performance indicator with a threshold value, generate a feedback signal based on the comparison, and transmit the generated signal to the user interface 306. The user interface 306 may be used to receive a tactile or audio signal, or to visualize the performance indicators e.g. over time or in relation to the movement class. In the embodiment described in FIG. 3b, the system 30 may also comprise a client 330 connected to the server, to realize the visualization.

The units and circuits described above with reference to FIGS. 3a-b may be logical units, separate physical units or a combination of both logical and physical units.

The above mentioned and described embodiments are only given as examples and should not be limiting. Other solutions, uses, objectives, and functions within the scope of the accompanying patent claims may be possible.

The invention claimed is:

1. A method for determining a value of a performance indicator for a periodic movement performed by a human or an animal, the method comprising:
   receiving (210) time series data from an inertial sensor sensing the periodic movement of the human or animal;
   partitioning (220) the received time series data into periods of the movement;
   transforming (230) the time series data of each period into a data representation of a defined size,
   classifying (240) each period into a movement class based on the data representation and a statistical model comprising a Markov chain of multivariate Gaussian distributions for each movement class; and determining (250) a value of a performance indicator for at least one period of the movement, based on the data representation and on the movement class of the at least one period.

2. The method according to claim 1, wherein the performance indicator comprises a level of consistency for at least two periods classified into a same movement class, and wherein a value of the level of consistency is determined based on a variance of the data representation for the at least two periods.

3. The method according to claim 1, wherein the performance indicator comprises a frequency of movement, and wherein a value of the frequency of movement is determined by dividing an amount of subsequent periods classified into a same movement class with the time lapsed during said subsequent periods.

4. The method according to claim 1, wherein the performance indicator comprises a level of symmetry for a period classified into a movement class corresponding to a symmetric movement, and wherein a value of the level of symmetry is determined based on a variance of the data representation of the period and a cyclically phase-shifted and mirrored data representation of the period.

5. The method according to claim 1, wherein the performance indicator comprises a propulsion indicator for a period of a specific movement class, and wherein determining (250) a value of the propulsion indicator comprises:

determining a first time value corresponding to a sequence of positive forward acceleration values in the data representation of the period, determining a second time value corresponding to the time of the period, and dividing the first time value with the second time value.

6. The method according to claim 1, the method further comprising:

retrieving (260) information related to at least one of a pulse beat and a position of the human or the animal when performing the periodic movement, wherein the value of the performance indicator is determined based also on the retrieved information.

7. The method according to claim 1, wherein the periodic movement is one of the group consisting of: a movement of a cross-country skier using a classic ski technique, a movement of a cross-country skier using a skate technique, a movement of a runner, a person performing a rehab programme movement, and a movement of a horse.

8. The method according to claim 1, further comprising:

comparing (270) the determined value of the performance indicator with a threshold value; and transmitting (280) a signal generated based on the comparison to the human or animal performing the periodic movement via a user interface.

9. The method according to claim 8, wherein the signal is at least one of an audio signal, a tactile signal, and a visual signal.

10. The method according to claim 1, wherein partitioning (220) the received time series data comprises low-pass filtering the received time series data to identify limits between each period of the movement, and partitioning the received time series data according to the identified limits.

11. The method according to claim 1, wherein transforming (230) the time series data of each period comprises low-pass filtering the time series data of each period to reduce noise, and re-sampling the low-pass filtered data to form a data representation of a defined size.

12. A system (30) for determining a value of a performance indicator for a periodic movement performed by a human or an animal, the system comprising:

an inertial sensor (305a) that senses the periodic movement of the human or animal;

a communication unit (304); and a processing circuit (302) connected to the communication unit (304), wherein the communication unit is configured to receive time series data transmitted from the inertial sensor, and wherein the processing circuit is configured to:

partition the received time series data into periods of the movement, transform the time series data of each period into a data representation of a defined size, classify each period into a movement class based on the data representation and a statistical model comprising a Markov chain of multivariate Gaussian distributions for each movement class, and generate a performance indicator for at least one period of the movement, based on the data representation and on the movement class of the at least one period.

13. The system according to claim 12, further comprising:

at least one of a pulse beat sensor (305b) for sensing pulse beats of the human or the animal when performing the periodic movement; and a global positioning system (GPS) receiver device for determining a position of the human or the animal when performing the periodic movement, wherein the communication unit (304) is further configured to retrieve information related to a pulse beat from the pulse beat sensor and to a position from the GPS receiver device, and wherein the processing circuit (302) is configured to determine the value of the performance indicator based also on the retrieved information.

14. The system (30) according to claim 12, further comprising:

a user interface, and wherein the processing circuit (302) is further configured to compare the determined value of the performance indicator with a threshold value and to transmit a signal generated based on the comparison to the user interface.

15. The system according to claim 12, wherein the performance indicator comprises a level of consistency for at least two periods classified into a same movement class, and wherein the processing circuit is further configured to determine a value of the level of consistency based on a variance of the data representation for the at least two periods.

16. The system according to claim 12, wherein the performance indicator comprises a frequency of movement, and wherein the processing circuit is further configured to determine a value of the frequency of movement by dividing an amount of subsequent periods classified into a same movement class with the time lapsed during said subsequent periods.

17. The system according to claim 12,
wherein the performance indicator comprises a level of symmetry for a period classified into a movement class corresponding to a symmetric movement, and
wherein the processing circuit is further configured to determine a value of the level of symmetry based on a variance of the data representation of the period and a cyclically phase-shifted and mirrored data representation of the period.

18. The system according to claim 12,
wherein the performance indicator comprises a propulsion indicator for a period of a specific movement class, and
wherein the processing circuit is further configured to determine the value of the propulsion indicator by:
 determining a first time value corresponding to a sequence of positive forward acceleration values in the data representation of the period,
 determining a second time value corresponding to the time of the period, and
 dividing the first time value with the second time value.

19. The system according to claim 12, wherein the processing circuit is configured to partition the received time series data by low-pass filtering the received time series data to identify limits between each period of the movement, and by partitioning the received time series data according to the identified limits.

20. The system according to claim 12, wherein the processing circuit is configured to transform the time series data of each period by low-pass filtering the time series data of each period to reduce noise, and by re-sampling the low-pass filtered data to form a data representation of a defined size.

\* \* \* \* \*